Figure 1:
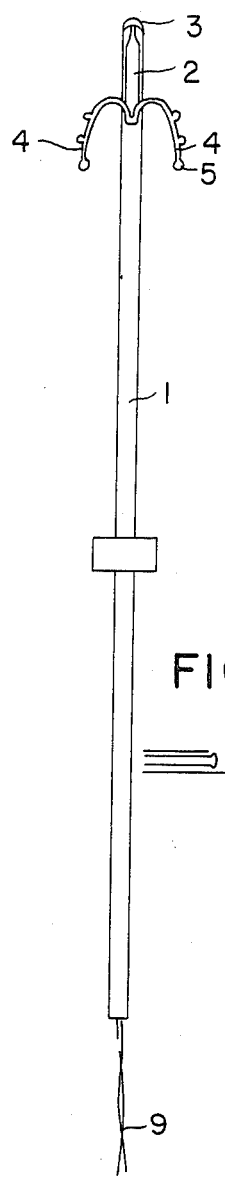

United States Patent [19]

van Os

[11] Patent Number: 4,690,136

[45] Date of Patent: Sep. 1, 1987

[54] ASSEMBLY OF INTRA-UTERINE CONTRACEPTIVE DEVICE AND INSERTOR

[75] Inventor: Willem A. A. van Os, Le Rouret, France

[73] Assignee: Akzo N.V., Arnhem, Netherlands

[21] Appl. No.: 807,980

[22] Filed: Dec. 12, 1985

[30] Foreign Application Priority Data

Dec. 21, 1984 [NL] Netherlands ............... 8403915

[51] Int. Cl.⁴ .............................................. A61F 5/46
[52] U.S. Cl. ...................................................... 128/130
[58] Field of Search ........................................... 128/130

[56] References Cited

U.S. PATENT DOCUMENTS

| | | | |
|---|---|---|---|
| 3,507,274 | 4/1970 | Soichet | 128/130 |
| 3,783,861 | 1/1974 | Abramson | 128/127 |
| 3,880,156 | 4/1975 | Hoff | 128/130 |
| 3,913,573 | 10/1975 | Gotnick | 128/130 |
| 3,918,444 | 11/1975 | Hoff et al. | 128/130 |
| 3,952,734 | 4/1976 | van Os et al. | 128/130 |
| 3,954,103 | 5/1976 | Garcia-Roel | 128/130 |
| 4,143,656 | 3/1979 | Holmes | 128/130 |

FOREIGN PATENT DOCUMENTS

| | | |
|---|---|---|
| 7402008 | 8/1975 | Netherlands . |
| 7802043 | 10/1978 | Netherlands . |
| 461348 | 2/1937 | United Kingdom . |

*Primary Examiner*—William R. Cline
*Assistant Examiner*—Richard R. Cole
*Attorney, Agent, or Firm*—William M. Blackstone

[57] ABSTRACT

The invention comprises an assembly of an intra-uterine contraceptive device and an insertor, whereby the contraceptive device is provided with a central stem and two or more flexible self-supporting arms; at least the said stem is accommodated in the insertor, and said insertor is at one end, over some distance, opened to form a groove or half-cylinder in such a way that the stem of the contraceptive device can be introduced and removed therefrom, said half-cylinder portion ending into a knob or thickening.

5 Claims, 8 Drawing Figures

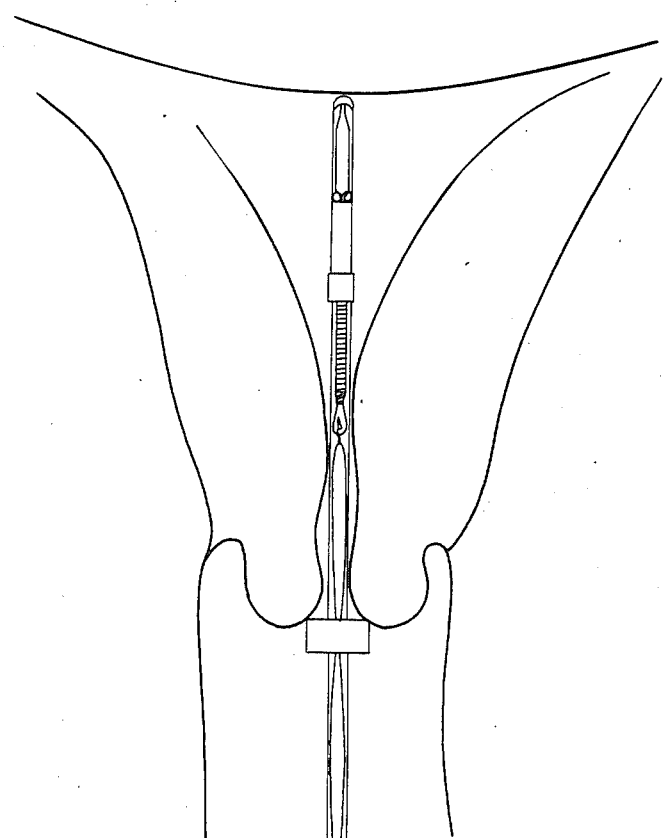
FIG. 7
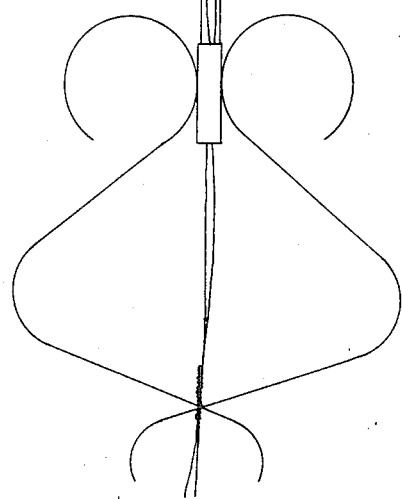

ASSEMBLY OF INTRA-UTERINE CONTRACEPTIVE DEVICE AND INSERTOR

The invention relates to an assembly of an intra-uterine contraceptive device and the corresponding insertor, the contraceptive device being provided with a central stem which at one of the ends merges into at least two flexible self-supporting arms, at least the stem being accommodated in the insertor with the aid of which the said contraceptive device can be fitted into the uterine cavity.

This type of assembly of a contraceptive device and corresponding insertor is known from, inter alia, Netherlands Patent Specification No. 173,707, where the contraceptive device described consists of an elongate stem which possesses two highly flexible self-supporting arms on one of its ends. These arms are attached to opposite sides of the stem and in the state of rest curve back toward the stem in such a way that the arms together form, the entire or partial periphery of an ellipse, with the stem as the long axis or a part of the long axis of the said ellipse.

This assembly of contraceptive device and corresponding insertor—the stem of the contraceptive device being fitted into the preferably tubular insertor—is now introduced into the uterus via the cervix. While passing through the cervix, the arms of the contraceptive device are compressed against the outside of the insertor.

Though, in the vast majority of patients, this method of introduction presents no problems and is found to be a very simple and convenient method, it is found, in a small number of patients—e.g. those who have never given birth—that it can cause a slight injury. The risk of infections, resulting therefrom, is then of course a particularly undesirable side-effect.

The present invention offers the physician, when inserting the contraceptive device, the free choice between the method wherein, during the introduction, the arms of the contraceptive device are compressed onto the outside of the insertor and the method wherein the entire contraceptive device—including the arms—is located in the inside of the insertor.

To this effect, the invention comprises an assembly of intra-uterine contraceptive device and corresponding insertor characterised in that the end of the insertor is, over some distance, opened to form a groove, half-cylinder or almost half-cylinder in such a way that the stem of the contraceptive device can be introduced therein and removed therefrom, the groove of half-cylinder portion of the insertor merges, on the introduction site, into a knob or thickening, and the arms of the contraceptive device—when extended along the length of the stem—can also be suitably introduced into the interior of the insertor.

The invention is illustrated in more detail in the drawings:

FIG. 1 provides a front view of a contraceptive device in an insertor (1) of opaque material. The insertor (1) is provided, at its end, with a groove or half-cylinder portion (2) and a thickening or stiffening (3). The contraceptive device (of the type shown in FIG. 4), the stem of which is fitted, non-visibly, into the insertor possesses two arms (4) which are each provided with a knob (5) at the end.

Figure 2:
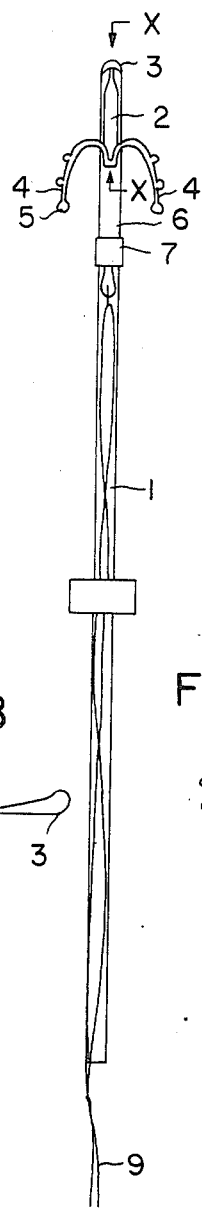

FIG. 2 shows a variant of the assembly of contraceptive device and insertor of FIG. 1. The insertor (1) is produced of transparent material and the half-cylinder portion (2) is here a part of an attachment (6) which is fitted via a socket (7) onto the end of the insertor (1). The stem of the contraceptive device (of the type of FIG. 4) is fitted into the insertor carrying the attachment 6.

Figure 3:
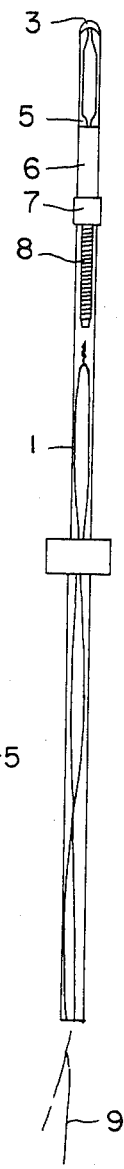
Figure 4:
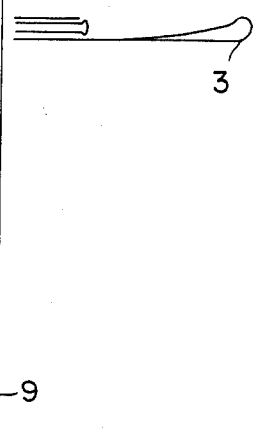

FIG. 3 shows the contraceptive device of FIG. 4 in a different position from that in the preceding FIGS. 1 and 2. The contraceptive device is now fitted, in its entirety, into the insertor (1). Only the knobs (5) at the end of the arms of the contraceptive device prevent the latter from slipping further into the insertor.

FIG. 4 shows a front view of a preferred contraceptive device. The stem (8), which in the drawing is wrapped with a copper wire, is provided, at one of the ends, with two arms which are embedded in about a direct line with the stem. In the rest state, the arms are, in this embodiment, bent backward in the direction of the stem. The contraceptive device is moreover provided with a removal thread (9).

Figure 8:
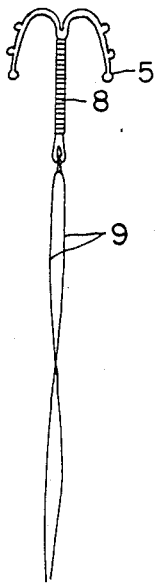

FIG. 8 shows a longitudinal section of the half-cylinder portion of FIG. 2 (along the axis X—X). The figure shows a preferred feature of the groove or half-cylinder portion, viz. the bottom of the groove or half-cylinder portion goes up towards the thickening (3) in order to ensure an easy release of the contraceptive device out of the groove or half-cylinder portion of the insertor.

The assembly of contraceptive device and insertor according to the invention is sterilised and then packaged in the form shown in FIGS. 1 and 2. This ensures that the contraceptive device does not lose its "memory" (the shape which it assumes in the rest state).

Figure 5:
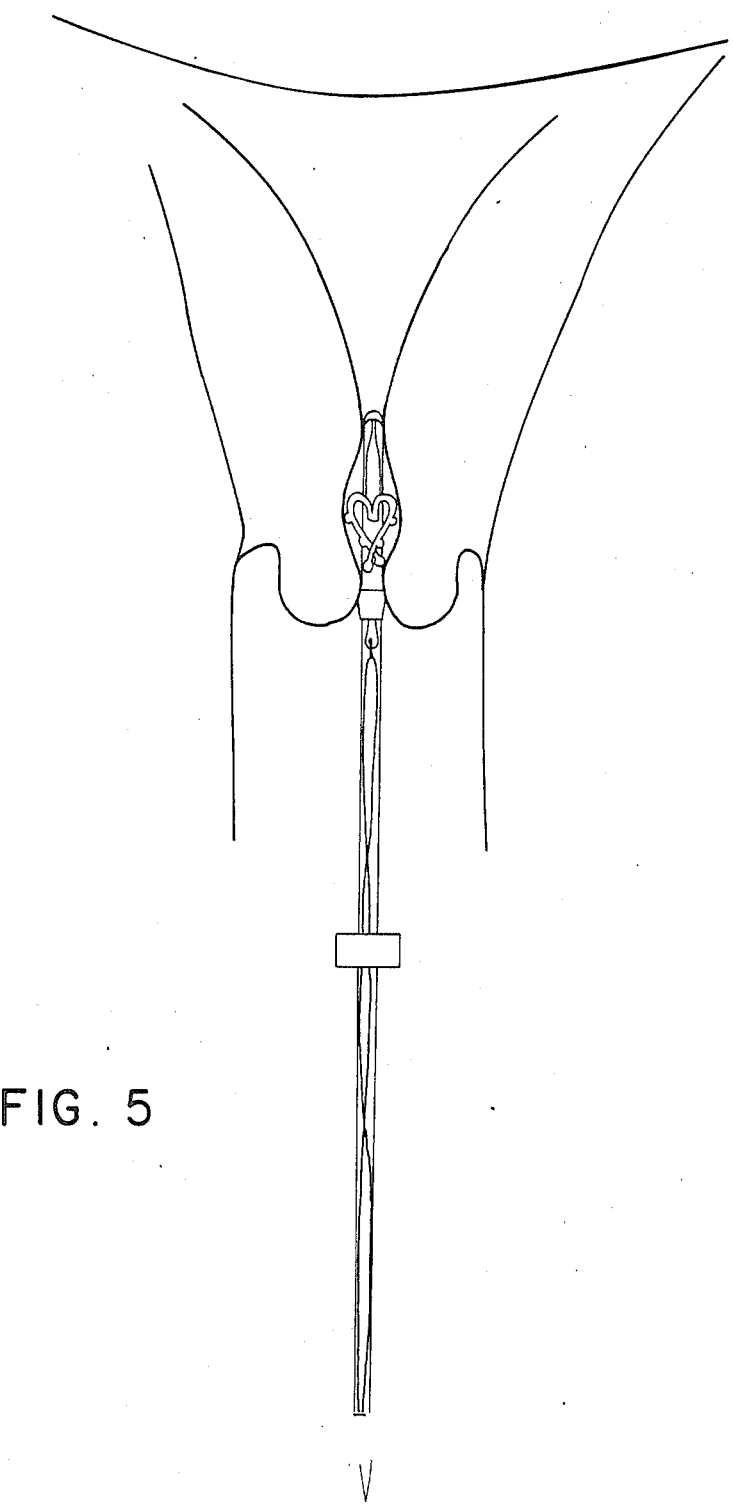

The assembly according to the invention can now be introduced in two ways. The method which requires no further preparation whatsoever is illustrated in FIG. 5. The assembly according to FIG. 2 is fitted directly, via the cervix, into the uterus. When the thickened end (3) of the insertor reaches the upper face of the uterus wall, the contraceptive device can be pushed up, by means of a plunger fitted in the insertor into the (open) half-cylinder portion of the insertor. The insertor can now directly be withdrawn, leaving the contraceptive device in the uterus. This method of releasing the contraceptive device is illustrated in FIG. 6.

A different method of introduction, which is preferred by some patients, is illustrated in FIG. 7. The assembly of contraceptive device and insertor according to FIG. 2 is, for this purpose, first brought into the state indicated in FIG. 3.

This can be achieved in a simple manner by pulling the contraceptive device further into the insertor with the aid of the device's removal thread. To prevent the contraceptive device from shooting too far into the tube, it is preferred to provide the end of the arms of the contraceptive device with a knob or thickening.

Figure 6:
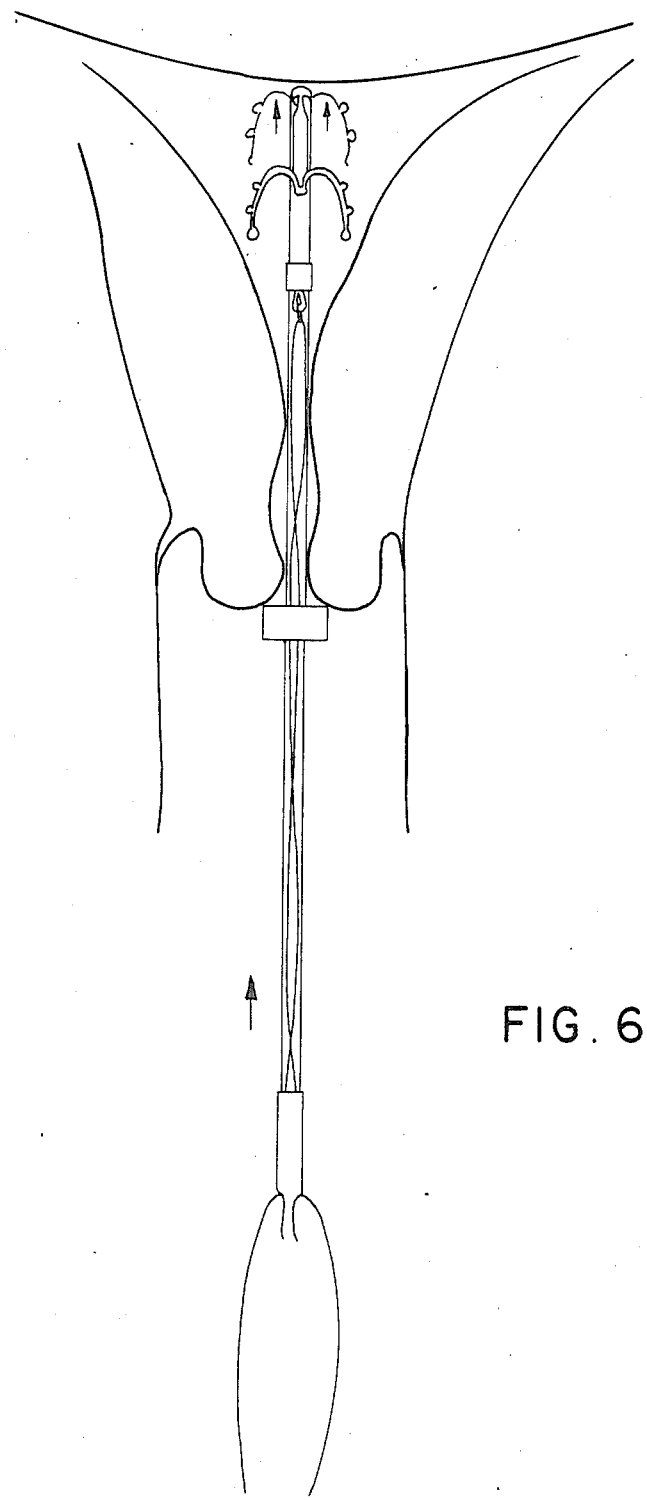

The contraceptive device which is fitted into the insertor in this manner has to be removed from the insertor with the aid of a plunger (see FIG. 6).

The insertor according to the invention differs in principle from the conventional insertors in respect of the presence of the (open) half-cylinder portion or groove at the end of the insertor.

This novel half-cylinder portion functions not only as a probe but also has the advantage that during the removal of the contraceptive device from the insertor less pressure has to be exerted on the uterus wall.

The contraceptive device which is used in the present invention consists of a stem and at least two flexible arms which are attached at one of the ends of the stem.

Preferably, the two arms are attached to the stem in a direct or approximately direct line with along the the stem. However, this is not essential.

Intra-uterine contraceptive devices which in principle can be used in the present invention have, for example, the shape of a "Y", a "T" or an anchor.

The preferred contraceptive device for use in the assembly according to the invention has two highly flexible arms embedded at one of ends of the stem in a direct or approximately direct line with the stem, these arms being provided at the end with a knob or thickening and, in the rest state, bent back in the direction of the stem in such a way that the portion of the arms runs roughly parallel to the stem, or the arms together form a kind of ellipse with the stem as the long axis.

The contraceptive device can moreover contain biologically active substances which are slowly released over the entire period or a certain period of use.

Biologically active substances which can be used are substances which prevent fertilisation, substances which destroy semen, substances which prevent haemorrhaging, anti-inflammatory substances etc.

Preferably, the stem of the contraceptive device (or other parts of the device) can moreover be wrapped with a copper wire or a copper wire with silver core, which enhances the fertilisation-preventing properties of the contraceptive device.

What is claimed is:

1. An assembly comprising an intra-uterine contraceptive device and a corresponding insertor for carrying the contraceptive device into the uterine cavity, the contraceptive device being provided with a central stem which at one of the ends merges into at least two flexible self-supporting arms, at least the stem of said contraceptive device being accommodated coaxially within the insertor when introducing the contraceptive device into the uterine cavity, said insertor comprising an elongated member having a hollow section at least at one end thereof formed by a substantially cylindrical wall and wherein a portion of said cylindrical wall is removed to form an opening in the side thereof located at the hollow section near or immediately adjacent to the end of the said member, the opening being of such a size and shape whereby the stem of the contraceptive device can be introduced therein and removed therefrom, and whereby the arms of the contraceptive device when extended along the length of the stem can also be suitably introduced into the interior of the insertor, the edge of said opening being smooth and merging at or near the end of said member to form a bulbous end portion having a smooth end surface, whereby said insertor having said contraceptive device accommodated therein can easily be inserted into the uterine cavity through the cervix and wherein said bulbous end portion acts as a ramp for the contraceptive device as it is removed from the insertor and deposited into the uterine cavity.

2. The assembly of claim 1, wherein the end of said member comprising the hollow section containing said opening, which is the end that carries the contraceptive device into the uterine cavity, comprises an attachment that is removably fixed to an elongated member.

3. An insertor for carrying an intra-uterine contraceptive device into the uterine cavity, comprising an elongated member having a hollow section at least at one end thereof formed by a substantially cylindrical wall and wherein a portion of said cylindrical wall is removed to form an opening in the side thereof located at the hollow section near or immediately adjacent to the end of said member having the hollow section, the opening being of such a size and shape whereby the stem of a contraceptive device provided with a central stem that at one end merges into at least two flexible self-supporting arms can be introduced therein and removed therefrom, the edge of said opening being smooth and merging at or near the end of said member to form a bulbous end portion having a smooth end surface, whereby said insertor with the contraceptive device accommodated therein can easily be inserted into the uterine cavity through the cervix and wherein said bulbous end portion acts as a ramp for the contraceptive device as it is removed from the insertor and deposited into the uterine cavity, said hollow section having an interior adjacent to said opening opposite the end surface being of such a shape to accommodate the stem of said contraceptive device coaxially therein and to accommodate, in addition, the arms of the contraceptive device when extended along the length of the stem.

4. The insertor of claim 3, wherein the end of said member comprising the hollow section containing said opening, which is the end that carries the contraceptive device into the uterine cavity, comprises an attachment that is removably fixed to an elongated member.

5. An attachment for use in an intra-uterine contraceptive device insertion assembly for carrying an intra-uterine contraceptive device into the uterine cavity, comprising an elongated member having a hollow section at least at one end thereof formed by a substantially cylindrical wall and wherein a portion of said cylindrical wall is removed to form an opening in the side thereof located at the hollow section near or immediately adjacent to the end of said member having the hollow section, the opening being of such a size and shape whereby the stem of a contraceptive device provided with a central stem that at one end merges into at least two flexible self-supporting arms can be introduced therein and removed therefrom, the edge of said opening being smooth and merging at or near the end of said member to form a bulbous end portion having a smooth end surface, whereby said insertor with the contraceptive device accommodated therein can easily be inserted into the uterine cavity through the cervix, and wherein said bulbous end portion acts as a ramp for the contraceptive device as it is removed from the insertor and deposited into the uterine cavity, said hollow section having an interior adjacent to said opening opposite the end surface being of such a shape to accommodate the stem of said contraceptive device coaxially therein and to accommodate, in addition, the arms of the contraceptive device when extended along the length of the stem.

* * * * *